United States Patent [19]
Hartke et al.

[11] Patent Number: 6,156,799
[45] Date of Patent: *Dec. 5, 2000

[54] METHOD OF INCREASING BONE VOLUME USING NON-NATURALLY-OCCURRING FP SELECTIVE AGONISTS

[75] Inventors: James Richard Hartke, West Chester; Mark Walden Lundy, Cincinnati; Mitchell Anthony deLong, West Chester, all of Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 09/148,105

[22] Filed: Sep. 4, 1998

Related U.S. Application Data
[60] Provisional application No. 60/058,306, Sep. 9, 1997.

[51] Int. Cl.$^7$ ....................... A61K 31/557; C07C 405/00
[52] U.S. Cl. ............................................. 514/573; 560/121
[58] Field of Search ............................ 514/573; 554/117, 554/214; 560/121; 424/449

[56] References Cited

U.S. PATENT DOCUMENTS

| | | | |
|---|---|---|---|
| 4,621,100 | 11/1986 | Lund et al. | 514/573 |
| 5,310,759 | 5/1994 | Bockman | 514/573 |
| 5,409,911 | 4/1995 | Tyler et al. | 514/91 |
| 5,703,108 | 12/1997 | Cameron et al. | 514/382 |
| 5,747,660 | 5/1998 | Orlicky | 536/23.5 |

FOREIGN PATENT DOCUMENTS

WO 93/15767  8/1993  WIPO ............................ A61K 47/34

OTHER PUBLICATIONS

Griffin et al. FP prostaglandin receptors mediating inositol phosphates generation and calcium mobilization in Swiss 3T3 cells: A pharmacological study. J. Pharmac. And Exper. Therapeut. 281 (2), pp. 845–854, (May 1997).

Woodiel, F.L., Fall, P.M., Raisz, L.G., "Anabolic Effects of Prostaglandins in Cultured Fetal Rat Calvariae: Structure–Activity Relations and Signal Transduction Pathway", *Journal of Bone and Mineral Research*, vol. 11, No. 9, (1996).

Wada, S., Yasutomo, Y., Kosano, H. Kugai, N., Nagata, N., "The Effect of $PGF_{2\alpha}$ On Parathyroid Hormone–Stimulated Cyclic AMP Production in Mouse Osteoblastic Cell, $MC3T3E_1$", *Biochimica et Biophysica Acta*, vol. 1074, pp. 182–188, (1991).

Collins, D.A., Chambers, T.J., "Effect of Prostaglandins $E_1$, $E_2$, $F_{2\alpha}$ on Osteoclast Formation in Mouse Bone Marrow Cultures", *Journal of Bone and Mineral Research*, vol. 6, No. 2, (1991).

Ma, Y.F., Li, X.J., Jee, W.S.S., McOsker, J., Liang, G., Setterberg, R., Chow, S.Y., "Effects of Prostglandin $E_2$ and $F_{2\alpha}$ on the Skeleton of Osteopenic Ovariectomized Rats", *Bone*, vol. 17, No. 6, pp. 549–554 (Dec. 1995).

Raisz, L.G., Alander, C.B., Fall, P.M., Simmons, H.A., "Effects of Prostaglandin $F_{2\alpha}$ on Bone Formation and Resorption in Cultured Neonatal Mouse Calvariae: Role of Prostaglandin $E_2$ Production", *Endocrinology*, vol. 126, No. 2 (1990).

Woodward, D.F., Lawrence, R.A., "Identification of a Single (FP) Receptor Associated with Prostanoid–Induced $Ca^{2+}$ Signals in Swiss 3T3 Cells", *Biochemical Pharmacology*, vol. 47, No. 9, pp. 1567–1574, (1994).

Watanabe, T., Nakao, A., Emerling, D., Hashimoto, Y., Tsukamoto, K., Hoie, Y., Kinoshita, M., Kurokawa, K., "Prostaglandin $F_{2\alpha}$ Enhances Tyrosine Phosphorylation and DNA Synthesis Through Phospholipase C–coupled Receptor Via $Ca^{2+}$–dependent Intracellular Pathway in NIH–3T3 Cells", *The Journal of Biological Chemistry*, vol. 269, No. 26, Issue of Jul. 1, pp. 17619–17625, (Jul. 1994).

Ito, S., Sakamoto, K., Mochizuki–Oda, N., Ezashi, T., Miwa, K., Okuda–Ashitaka, E., Shevchenko, V.I., Kiso, Y., Hayaishi, O., "Prostaglandin $F_{2\alpha}$ Receptor is Coupled to Gq in cDNA–transfected Chinese Hamster Ovary Cells", *Biochemical and Biophysical Research Communications*, vol. 200, No. 2, pp. 756–762, (Apr. 1994).

Hakeda, Y., Shiokawa, M., Mano, H., Kameda, T., Raisz, L.G., Kumegawa, T., "Prostaglandin $F_{2\alpha}$ Stimulates Tyrosine Phosphorylation and Mitogen–Activated Protein Kinase in Osteoblastic MC3T3–E1 Cells via Protein Kinase C Activation", *Endocrinology*, vol. 138, No. 5 (May 1997).

Ida, R., Lee, A., Huang, J., Brandi, M.L., Yamaguchi, D.T., "Prostaglandin–Stimulated Second Messenger Signaling in Bone–Derived Endothelial Cells is Dependent on Confluency in Culture", *Journal of Cellular Physiology*, vol. 160, pp. 585–595, (1994).

Bergmann, P., Schoutens, A., "Prostaglandins and Bone", *Bone*, vol. 16, No. 4, pp. 485–488, (Apr. 1995).

Yamaguchi, D.T., Green, J., Kleeman, C.R., Muallem, S., "Prostaglandins Enhance Parathyroid Hormone–Evoked Increase in Free Cytosolic Calcium Concentration in Osteoblast–Like Cells", *Cell Calcium*, vol. 12, pp. 609–622, (1991).

Norrdin, R.W., Jee, W.S.S., High, W.B., "The Role of Prostaglandins in Bone In Vivo", *Prostaglandins Leukotrienes and Essential Fatty Acids*, vol. 41, pp. 139–149, (1990).

(List continued on next page.)

*Primary Examiner*—Ardin H. Marschel
*Assistant Examiner*—Marjorie A. Moran
*Attorney, Agent, or Firm*—James C. Kellerman; Carl J. Roof; Mary Pat McMahon

[57] ABSTRACT

The present invention relates to novel methods of increasing bone volume comprising the administration of a non-naturally-occurring selective FP agonist to a subject in need of such treatment. This invention further relates to a method of treating or preventing bone disorders comprising the administration of a non-naturally-occurring selective FP agonist to a subject in need of such treatment.

16 Claims, No Drawings

OTHER PUBLICATIONS

Flanagan, A.M., Chambers, T.J., "Stimulation of Bone Nodule Formation in Vitro by Prostaglandins $E_1$ and $E_2$", *Endocrinology*, vol. 130, No. 1 (1992).

Toriyama, K., Morita, I., Murota, S.–i., "The Existence of Distinct Classes of Prostaglandin $E_2$ Receptors Mediating Adenylate Cyclase and Phospholipase C Pathways in Ostoeblastic Clone MC323–$E_1$", *Prostaglandins Leukotrienes and Essential Fatty Acids*, vol. 46, pp. 15–20, (1992).

"Lutalyse®", *Veterinary Pharmaceuticals and Biologicals*, $8^{th}$ Edition, pp. 1066–1069, (1993 & 1994).

Fall, P.M., Breault, D.T., Raisz, L.G., "Inhibition of Collagen Synthesis by Prostaglandins in the Immortalized Rat Osteoblastic Cell Line Py1a: Structure–Activity Relations and Signal Transduction Mechanisms", *Journal of Bone and Mineral Research*, vol. 9, No. 12, pp. 1935–1943, (1994).

Kawaguchi, H., Pilbeam, C.C., Harrison, J.R., Raisz, L.G., "The Role of Prostaglandins in the Regulation of Bone Metabolism", *Clinical Orthopaedics and Related Research*, No. 313, pp. 36–46, (1995).

Quarles, L.D., Siddhanti, S.R., "Guanine Nucleotide Binding–Protein Coupled Signaling Pathway Regulation of Osteoblast–Mediated Bone Formation", *Journal of Bone and Mineral Research*, vol. 11, No. 10, pp. 1375–1383, (1996).

Nemoto, KI., Bernecker, P.M., Pilbeam, C.C., Raisz, L.G., "Expression and Regulation of Prostaglandin F Receptor mRNA in Rodent Osteoblastic Cells", *Prostaglandins*, vol. 50, pp. 349–358, (Nov. 1995).

Tamura, K., Nemoto, K., Pilbeam, C.C., Raisz, L.G., "Expression and Regulation of Prostaglandin F Receptor mRNA in Rodent Osteoblastic Cells", *Abstract T352 (as noted) ASBMR $19^{th}$ Annual Meeting*, p. S189, No Month or Year Found.

METHOD OF INCREASING BONE VOLUME USING NON-NATURALLY-OCCURRING FP SELECTIVE AGONISTS

CROSS REFERENCE

This application claims priority under Title 35, United States Code 119(e) from Provisional Application Serial No. 60/058,306, filed Sep. 9, 1997.

TECHNICAL FIELD

The present invention relates to novel methods of increasing bone volume comprising the administration of a non-naturally-occurring selective FP agonist to a subject in need of such treatment. This invention further relates to a method of treating or preventing bone disorders comprising the administration of a non-naturally-occurring selective FP agonist to a subject in need of such treatment.

BACKGROUND OF THE INVENTION

In osteoporotics an imbalance in the bone remodeling process develops in which bone is resorbed at a rate faster than it is being made. Although this imbalance occurs to some extent in most individuals, both male and female, as they age, it is much more severe and occurs at a younger age in osteoporotics, particularly those who develop the post menopausal form of the condition. Accelerated bone loss may also result from drug administration, such as corticosteroids; prolonged bedrest; disuse of a limb; and microgravity. A consequence of this loss of bone is the complete removal of trabeculae and a deterioration of bone architecture such that the remaining bone is disproportionately decreased in strength.

It is thought that to completely return the bone to normal strength, new trabeculae should be formed to restore architecture and increase bone mass. It is further thought that when the restoration of normal architecture is associated not only with an increase in the strength, but also a return to normal stiffness and shock absorbing capability, the bone is less likely to fracture. Subjects suffering from other bone disorders such as osteoarthritis, Paget's disease, periodontal disease, and fractures may also benefit from treatments that restore bone mass and normal architecture to bone.

There have been many attempts to treat bone disorders with a variety of pharmacologic agents with the goal being to either slow further bone loss or to produce a net gain in bone mass. There are antiresorptive agents, such as bisphosphonates, which slow further bone loss, and there are anabolic agents, such as PTH, fluoride, and prostaglandins, which build bone. But, none of these agents build bone that is substantially similar, i.e. structurally or architecturally, to the type of bone lost.

PTH and prostaglandins, especially prostaglandins of the E series (e.g. $PGE_2$), are known to be potent stimulators of bone resorption and formation. The acceleration in turnover seen with these known bone anabolic agents may be detrimental to an already osteoporotic skeleton since the increased resorption may cause perforation and loss of trabeculae, or may weaken the existing trabecular structure. In addition, increased resorption may occur in cortical bone. These effects may in turn lead to increased fracture incidence at some sites.

$PGF_{2\alpha}$ has also been shown to be a stimulator of bone resorption, but it is not as potent as $PGE_2$. It has been suggested that some of the effects of $PGF_{2\alpha}$ on bone resorption, formation, and cell replication may be mediated by an increase in endogenous $PGE_2$ production. Furthermore, in vitro data with FP agonists have shown a decrease in collagen synthesis in osteoblastic cell lines, suggesting FP agonists would not be effective at increasing bone mass in vivo. Tamura, et al., J. Bone Min. Rsch., Supp. Vol. 5189, T352 (1997).

Prostaglandins, in addition, have several drawbacks which limit their desirability for systemic administration. For example, although prostaglandins are characterized by their activity at a particular prostaglandin receptor, their activity is not limited to any one prostaglandin receptor. Thus, systemic administration of prostaglandins is known to cause side effects such as inflammation, as well as surface irritation, smooth muscle contraction, bronchoconstriction, and vasoconstriction. Systemic administration of non-selective prostaglandin analogs can likewise cause side effects.

Thus, there is a continuing need to develop methods of replacing bone that result in bone that is substantially similar, structurally and architecturally, to the type of bone lost.

SUMMARY OF THE INVENTION

It has been surprisingly found that the systemic administration of non-naturally-occurring selective FP agonists results in a bone anabolic effect. It has been further surprisingly found that the quality of bone formed by the administration of non-naturally-occurring selective FP agonists is superior to that formed by the administration of other bone anabolic agents, including prostaglandins of the E series. Accordingly, the present invention is directed to methods of increasing bone volume by administering to a subject a safe and effective amount of a non-naturally-occurring selective FP agonist. Particularly preferred non-naturally-occurring FP agonists are selective for the FP receptor over other excitatory prostaglandin receptors in a ratio of at least about 1:10, more preferably at least about 1:20, and most preferably at least about 1:50. Still more preferred non-naturally-occurring FP agonists are selective for FP receptors over all other prostanoid receptors in a ratio of at least about 1:10, more preferably at least about 1:20, and most preferably at least about 1:50.

It has been further found that non-naturally-occurring selective FP agonists increase trabecular number (through formation of new trabeculae), increase bone volume and mass while maintaining a more normal bone turnover rate, and increase formation at the endosteal surface without removing bone from the existing cortex. Accordingly, the present invention is directed to methods of increasing trabecular number by administering to a subject a safe and effective amount of a non-naturally-occurring selective FP agonist.

It has similarly been found that non-naturally-occurring selective FP agonists are useful in treating bone disorders. Accordingly, the present invention is directed to methods of treating bone disorders by administering to a subject a safe and effective amount of a non-naturally-occurring selective FP agonist.

DETAILED DESCRIPTION OF THE INVENTION

The present invention is directed to methods of increasing bone volume, methods of increasing trabecular number, and methods of treating bone disorders by administering to a subject a safe and effective amount of a non-naturally-occurring selective FP agonist.

Definitions and Usage of Terms

As used herein, "bone disorder" means the need for bone repair or replacement. Conditions in which the need for bone repair or replacement may arise include: osteoporosis (including post menopausal osteoporosis, male and female senile osteoporosis and corticosteroid induced osteoporosis), osteoarthritis, Paget's disease, osteomalacia, multiple myeloma and other forms of cancer, prolonged bed rest, chronic disuse of a limb, anorexia, microgravity, exogenous and endogenous gonadal insufficiency, bone fracture, non-union, defect, prosthesis implantation and the like.

As used herein, "bone turnover rate" means the amount of bone resorption and formation per unit time measured or estimated using incorporation of fluorescent labels into bone, fluorescent and bright field microscopy, and histomorphometric techniques or by measurement of bone metabolism markers. For example, a subject may resorb and replace (turn over) approximately 3% of its skeleton over a 3 month period. A further description of histomorphometric techniques can be found in Bone Histomorphometry, 1994, by Eriksen et al., Raven Press.

As used herein, "bone volume" refers to the percentage of the bone occupied by a mineralized matrix. Measurement or estimation of the mineralized matrix volume can be accomplished using histomorphometry, computed tomography, or magnetic resonance imaging. Two dimensional measurements may be used to estimate the three dimensional volume. A further description of histomorphometric techniques can be found in Bone Histomorphometry, 1994, by Eriksen et al., Raven Press.

As used herein, "excitatory prostaglandin receptor" means prostanoid receptors which cause contraction of smooth muscle or release of internal calcium stores. Such receptors include but are not limited to FP, $EP_1$, $EP_3$, $TP_1$, and $TP_2$.

As used herein, "FP" is an abbreviation for F prostanoid.

As used herein, "FP agonist" means a compound with affinity for the FP receptor that results in measurable biological activity (including but not limited to an elevation in intracellular calcium or the contraction of smooth muscle) in cells, tissues, or organisms which contain the FP receptor. Whole cell, tissue, and organism assays which demonstrate FP activity of compounds are well known in the art. One particularly useful assay is the R-SAT™ Assay described by Brann, et al. in *J. Biomole. Screen*, Vol. 1, Number 1, 1996.

As used herein, "FP receptor" means known human FP receptors, their splice variants, and undescribed receptors that preferentially bind $PGF_{2\alpha}$. A human FP receptor is disclosed in PCT Publication WO 95/00551.

As used herein, "measurable" means the biologic effect is both reproducible and significantly different from the baseline variability of the assay.

As used herein, "non-naturally-occurring" means an agent that is not biologically derived in mammals.

As used herein, "prostaglandin analog" refers to a non-naturally-occurring compound which is structurally similar to a prostaglandin.

As used herein, "prostaglandin analog" refers to a non-naturally-occurring compound which is structurally similar to a prostaglandin.

As used herein, "prostaglandin receptor" or "prostanoid receptor" means a naturally-occurring protein that binds prostaglandins, which when bound alters the function of a cell. Prostaglandin receptors may be characterized as either excitatory or relaxant. Such receptors include but are not limited to FP, $EP_1$, $EP_2$, $EP_3$, $EP_4$, DP, IP, $TP_1$ and $TP_2$. These receptors are further discussed by Coleman et al., in Pharmacological Reviews, 1994, Volume 6, No. 2, pages 205–229.

As used herein, "selective" means having an activation preference for a specific receptor over other receptors which can be quantified based upon whole cell, tissue, or organism assays which demonstrate receptor activity, such as the R-SAT™ Assay disclosed above. A compound's selectivity is determined from a comparison of its $EC_{50}$ (or $ED_{50}$ if using an organism assay) at the relevant receptors. For example, a compound having an $EC_{50}$ of 8 nM at the FP receptor and an $EC_{50}$ of 80 nM at the $EP_1$ receptor has a selectivity ratio for the FP receptor over the $EP_1$ receptor of 1:10.

As used herein, "trabecular number" refers to the number of individual trabeculae of bone per unit volume of cancellous bone measured or estimated from a two dimensional representation or a three dimensional specimen using histomorphometry, computed tomography, or magnetic resonance imaging.

As used herein, "subject" means a living vertebrate animal such as a mammal (especially human) in need of treatment.

Compounds

Compounds useful in the present invention are non-naturally-occurring selective FP agonists. Particularly preferred non-naturally-occurring FP agonists are selective for the FP receptor over other excitatory prostaglandin receptors in a ratio of at least about 1:10, more preferably at least about 1:20, and most preferably at least about 1:50. Still more preferred non-naturally-occurring FP agonists are selective for FP receptors over all other prostanoid receptors in a ratio of at least about 1:10, more preferably at least about 1:20, and most preferably at least about 1:50.

Particularly useful non-naturally-occurring selective FP agonists are prostaglandin analogs. Examples of such compounds are prostaglandin analogs having the following general structure:

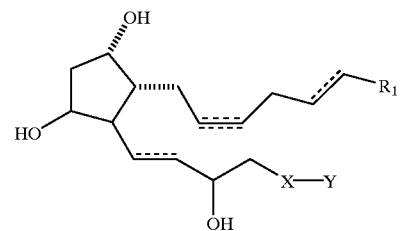

wherein:
$R_1$ is $CO_2H$, $C(O)NHOH$, $CO_2R_2$, $CH_2OH$, $S(O)_2R_2$, $C(O)NHR_2$, $C(O)NHS(O)_2R_2$, or tetrazole; characterized in that $R_2$ is alkyl, heteroalkyl, carbocyclic aliphatic ring, heterocyclic aliphatic ring, aromatic ring, or heteroaromatic ring;

X is $(CH_2)_n$, where n is 0 to 3, NH, S, or O; and

Y is a cycloalkyl or aromatic moiety, either substituted or unsubstituted.

Prostaglandin analogs of the above structure include: cloprostenol (Estrumate®), fluprostenol (Equimate®), tiaprost, alfaprostol, delprostenate, froxiprost, latanoprost, 13,14-dihydro-16-((3-trifluoromethyl)phenoxy)-16-tetranor prostaglandin $F_1\alpha$, 17-((3-trifluoromethyl)phenyl)-17-trinor-prostaglandin $F_2\alpha$, 13,14-dihydro-18-thienyl-18-dinor prostaglandin $F_1\alpha$ and their analogs.

Other prostaglandin analogs of the present invention include 9-alpha, 11-alpha, 15-alpha-trihydroxy-16-(3-chlorophenoxy)-omega-tetranor-prosta-4-cis-13-trans-dienoic acid and its analogs. Additional prostaglandin analogs are also disclosed in *CRC Handbook of Eicosanoids:*

*Prostaglandins and Related Lipids*, Volume I, *Chemical and Biochemical Aspects*, Part B. Ed. by Anthony L. Willis, CRC Press (Boca Raton, 1987) Table Four pp. 80–97 (incorporated herein by reference), and references therein.

Methods of Use

The compounds described above are useful in increasing bone volume, increasing trabecular number through formation of new trabeculae, increasing bone mass without increasing the bone turnover rate, and increasing formation at the endosteal surface without removing bone from the existing cortex. Additionally, the quality of bone formed by the administration of these compounds is superior to that formed by the administration of other bone anabolic agents, including prostaglandins of the E series. Bone quality refers to the combination of bone matrix (inorganic and organic), bone mass or volume, and bone architecture which impart overall strength and fracture resistance to bone. Accordingly, these compounds are further useful in the treatment and prevention of a variety of bone disorders.

The preferred routes of administration for increasing bone volume and treating bone disorders are transdermal and subcutaneous, e.g. injection or pellet. Other preferred routes of administration include oral, sublingual, and intranasal.

The dosage range for systemic administration of the non-naturally-occurring FP agonists of the present invention is from about 0.01 to about 1000 µg/kg body weight per day, preferably from about 0.05 to about 100 µg/kg per body weight per day, most preferably from about 0.1 to about 50 µg/kg body weight per day. Plasma levels are expected to be in the range of about 0.01 to about 500 ng/ml, more preferably from about 0.05 to 100 ng/ml, and most preferably from about 0.1 to 50 ng/ml.

While these dosages are based upon a daily administration rate, weekly or monthly accumulated dosages may also be used to calculate the clinical requirements. The non-naturally-occurring FP agonists of the present invention may be administered, based on a weekly dosage, more frequently than once daily. The non-naturally-occurring FP agonists of the present invention may also be administered, based on a weekly dosage, less frequently than once daily. Hence, the weekly dosage may be divided into 3, 4, 5, 6, or 7 daily dosages, preferably 5, 6, or 7 daily dosages.

Dosages may be varied based on the patient being treated, the condition being treated, the severity of the condition being treated, and the route of administration to achieve the desired effect.

It has been further discovered that prolonged delivery (also referred to as "prolonged administration") of the non-naturally-occurring FP agonist unexpectedly results in improved dose separation between side effects and the desired bone effect. As used herein, "prolonged delivery" or "prolonged administration" means that the total daily dosage is delivered into the subject's circulation over a period of at least about 6 hours and up to 24 hours. Preferred prolonged delivery periods are for at least about 12 hours and up to 24 hours. Examples of prolonged delivery include administration of the non-naturally-occurring FP agonist via a transdermal patch or a subcutaneous pump that delivers the total daily dosage over a twenty-four hour period.

It is believed that the flattening of the plasma concentration curve resulting from prolonged delivery mitigates side effects while maintaining bone efficacy. It is further believed that the administration of non-naturally-occurring FP agonists with extended half-lives will likewise result in a flattening of the plasma concentration curve without prolonging the administration.

The following non-limiting examples serve to further illustrate the use of the agents of the present invention.

EXAMPLE I

The FP agonist, fluprostenol, is administered to a 65 year old woman who has decreased bone mass and has been diagnosed with osteoporosis by her physician. She is treated daily with a transdermal patch that delivers 10 µg/kg fluprostenol over a 24 hour period. This treatment is continued for 24 months, at which time, vertebral bone mass is substantially increased compared to her vertebral bone mass at the onset of therapy as measured by dual energy X-ray absorptiometry (DXA).

EXAMPLE II

The FP agonist, fluprostenol, is administered to a 63 year old woman who has decreased bone mass and has been diagnosed with osteoporosis by her physician. She is treated with an implantable subcutaneous pump that delivers 10 µg/kg fluprostenol over a 24 hour period. This treatment is continued for 12 months, at which time, vertebral bone mass is substantially increased compared to her vertebral bone mass at the onset of therapy as measured by dual energy X-ray absorptiometry (DXA).

Pharmaceutical Formulations

Pharmaceutical formulations of the present invention comprise a safe and effective amount of the non-naturally-occurring FP agonist and a pharmaceutically acceptable carrier.

The phrase "safe and effective amount", as used herein means an amount of a compound or composition high enough to significantly positively modify the symptoms and/or condition to be treated, but low enough to avoid serious side effects (at a reasonable benefit/risk ratio), within the scope of sound medical judgment. The safe and effective amount of an agent for use in the method of the invention herein will vary with the particular condition being treated, the age and physical condition of the patient being treated, the severity of the condition, the duration of the treatment, the nature of concurrent therapy, the particular agent being employed, the particular pharmaceutically-acceptable excipients utilized, and like factors within the knowledge and expertise of the attending physician.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a subject. The term "compatible", as used herein, means that the components of the composition are capable of being commingled with the compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the subject being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a compound is basically determined by the way the compound is to be administered. The non-naturally-occurring FP agonist of the present invention may be administered systemically, including transdermally, orally and/or parenterally, including subcutaneous or intravenous injection, and/or intranasally.

The appropriate amount of the agent, preferably non-naturally-occurring FP agonist, to be used may be determined by routine experimentation with animal models. Such a model includes, but is not limited to, the intact and ovariectomized rat models of osteoporosis, the ferret, canine, and non human primate models of osteoporosis, as well as disuse models of osteoporosis.

A preferred method of administering non-naturally-occurring FP agonists is via transdermal delivery. Preferred transdermal dosage forms include transdermal patches, creams, ointments, gels and the like. Another preferred method of administering non-naturally-occurring FP agonists is via subcutaneous injection in a unit dosage form. Preferred unit dosage forms for injection include sterile solutions of water, physiological saline, or mixtures thereof. The pH of said solutions should be adjusted to about 7.4.

Other preferred dose forms include nasal, rectal, sublingual, and oral. Suitable carriers for injection or surgical implants include hydrogels, controlled- or sustained-release devises, polylactic acid, and collagen matrices. Implant devices may be coated with the non-naturally-occurring FP agonist. The non-naturally-occurring prostaglandin FP agonist may be dissolved in a buffer and may be mixed with a collagen gel which is then coated onto the porous end of the implant device.

Preferred oral forms include, for example liposomes, lipid emulsions, proteinaceous cages and pharmaceutically-acceptable excipients.

The term "pharmaceutically-acceptable excipients" as used herein includes any physiologically inert, pharmacologically inactive material known to one skilled in the art, which is compatible with the physical and chemical characteristics of the particular active ingredient selected for use. Pharmaceutically-acceptable excipients include, but are not limited to, polymers, resins, plasticizers, fillers, lubricants, binders, disintegrants, solvents, co-solvents, buffer systems, surfactants, preservatives, sweetening agents, flavoring agents, pharmaceutical grade dyes and pigments.

The following non-limiting examples illustrate formulations of the subject invention.

EXAMPLE III

Pharmaceutical formulations (compositions) in the form of tablets are prepared by conventional methods, such as mixing and direct compaction, formulated as follows

| Ingredient | Quantity (mg per tablet) |
| --- | --- |
| Fluprostenol | 5 |
| Microcystalline Cellulose | 100 |
| Sodium Starch Glycollate | 30 |
| Magnesium Stearate | 3 |

The above tablet administered orally once daily for six months substantially increases bone volume of a patient afflicted with Osteoporosis.

EXAMPLE IV

A pharmaceutical composition in liquid form is prepared by conventional methods, formulated as follows:

| Ingredient | Quantity |
| --- | --- |
| Cloprostenol | 5 mg |
| Phosphate buffered physiologic saline | 10 ml |
| Methyl paraben | 0.05 ml |

1.0 ml of the above composition administered subcutaneously once daily for six months substantially increases bone volume of a patient afflicted with osteoporosis.

While particular embodiments of the subject invention have been described, it would be obvious to those skilled in the art that various changes and modifications to the compositions disclosed herein can be made without departing from the spirit and scope of the invention.

What is claimed is:

1. A method of increasing bone volume, comprising administering to a subject a therapeutically effective amount of a synthetic FP agonist according to the general formula:

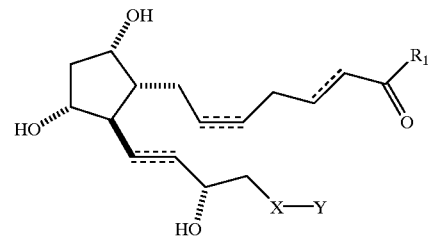

wherein:

$R_1$ is hydroxyl, a cationic salt moiety, a pharmaceutically-acceptable or biometabolizable amine or ester comprised of from about 1 to about 12 atoms;

X is $(CH_2)_n$, where n is 0 to 3, NH, S, or O; and

Y is a cycloalkyl or aromatic moiety, either substituted or unsubstituted.

2. The method of claim 1 wherein the synthetic FP agonist is selective for the FP receptor over other excitatory prostaglandin receptors.

3. The method of claim 2 wherein the synthetic FP agonist is further selective for the FP receptor over all other prostanoid receptors.

4. The method of claim 1 wherein the synthetic FP agonist is selected from the group consisting of cloprostenol, fluprostenol, tiaprost, alfaprostol, delprostenate, froxiprost, 9-alpha, 11-alpha, 15-alpha-trihydroxy-16-(3-chlorophenoxy)-omega-tetranor-prosta-4-cis-13-trans-dienoic acid, 17-((3-trifluoromethyl)phenyl-17-trinor-prostaglandin $F_{2\alpha}$, 13,14-dihydro-18-thienyl-18-dinor prostaglandin $F_1\alpha$, 13,14-dihydro-16-((3-trifluoromethyl)phenoxy)-16-tetranor prostaglandin $F_1\alpha$, latanoprost, and their analogs.

5. A method of increasing trabecular number, comprising administering to a subject a therapeutically effective amount of a synthetic FP agonist according to the general formula:

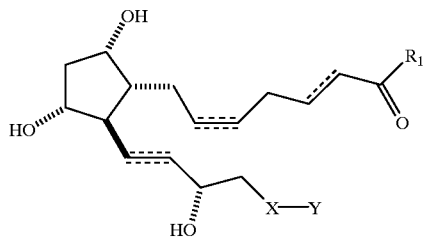

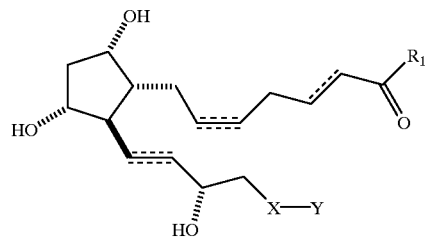

wherein:

R$_1$ is hydroxyl, a cationic salt moiety, a pharmaceutically-acceptable or biometabolizable amine or ester comprised of from about 1 to about 12 atoms;

X is (CH$_2$)$_n$, wherein n is 0 to 3, NH, S, or O; and

Y is a cycloalkyl or aromatic moiety, either substituted or unsubstituted.

6. The method of claim 5 wherein the synthetic FP agonist is selective for the FP receptor over other excitatory prostaglandin receptors.

7. The method of claim 6 wherein the synthetic FP agonist is further selective for the FP receptor over all other prostanoid receptors.

8. The method of claim 5, wherein the synthetic FP agonist is selected from the group consisting of cloprostenol, fluprostenol, tiaprost, alfaprostol, delprostenate, froxiprost, 9-alpha, 11-alpha, 15-alpha-trihydroxy-16-(3-chlorophenoxy)-omega-tetranor-prosta-4-cis-13-trans-dienoic acid, 17-((3-trifluoromethyl)phenyl-17-trinor-prostaglandin F$_2\alpha$, 13,14-dihydro-18-thienyl-18-dinor prostaglandin F$_1\alpha$, 13,14-dihydro-16-((3-trifluoromethyl)phenoxy)-16-tetranor prostaglandin F$_1\alpha$, latanoprost, and their analogs.

9. A method of treating a bone disorder, comprising administering to a subject a therapeutically effective amount of a synthetic FP agonist according to the general formula:

wherein:

R$_1$ is hydroxyl, a cationic salt moiety, a pharmaceutically-acceptable or biometabolizable amine or ester comprised of from about 1 to about 12 atoms;

X is (CH$_2$)$_n$, where n is 0 to 3, NH, S, or O; and

Y is a cycloalkyl or aromatic moiety, either substituted or unsubstituted.

10. The method of claim 9 wherein the synthetic FP agonist is selective for the FP receptor over other excitatory prostaglandin receptors.

11. The method of claim 10 wherein the synthetic FP agonist is further selective for the FP receptor over all other prostanoid receptors.

12. The method of claim 9 wherein the synthetic FP agonist is selected from the group consisting of cloprostenol, fluprostenol, tiaprost, alfaprostol, delprostenate, froxiprost, 9-alpha, 11-alpha, 15-alpha-trihydroxy-16-(3-chlorophenoxy)-omega-tetranor-prosta-4-cis-13-trans-dienoic acid, 17-((3-trifluoromethyl)phenyl-17-trinor-prostaglandin F$_{2a}$, 13,14-dihydro-18-thienyl-18-dinor prostaglandin F$_1\alpha$, 13,14-dihydro-16-((3-trifluoromethyl)phenoxy)-16-tetranor prostaglandin F$_1\alpha$, latanoprost, and their analogs.

13. The method of claim 9 wherein the synthetic FP agonist is administered transdermally.

14. The method of claim 9, wherein the bone disorder is selected from the group consisting of: osteoporosis, osteoarthritis, Paget's disease, osteomalacia, and bone fracture.

15. The method of claim 9, wherein the bone disorder is osteoporosis.

16. The method of claim 15, wherein the osteoporosis is post-menopausal osteoporosis.

* * * * *